US009925306B2

(12) United States Patent
Kim et al.

(10) Patent No.: US 9,925,306 B2
(45) Date of Patent: Mar. 27, 2018

(54) HYALURONIC ACID-CALCIUM PHOSPHATE COMPOSITE FOR GROWTH FACTOR SUPPORT AND METHOD FOR PRODUCING SAME

(71) Applicant: BIOALPHA INC., Seoul (KR)

(72) Inventors: Jung Ju Kim, Gyeonggi-Do (KR); Su Hyun Jung, Jeollabuk-Do (KR); Hyun Seung Ryu, Gyeonggi-Do (KR); Jun Hyuk Seo, Gyeonggi-Do (KR)

(73) Assignee: Bioalpha Inc., Seoul (KR)

( * ) Notice: Subject to any disclaimer, the term of this patent is extended or adjusted under 35 U.S.C. 154(b) by 0 days.

(21) Appl. No.: 15/401,455

(22) Filed: Jan. 9, 2017

(65) Prior Publication Data
US 2017/0112969 A1    Apr. 27, 2017

Related U.S. Application Data

(62) Division of application No. 14/388,013, filed as application No. PCT/KR2012/002397 on Mar. 30, 2012, now abandoned.

(30) Foreign Application Priority Data

Mar. 29, 2012    (KR) .......................... 10-2012-0032121

(51) Int. Cl.
*A61L 27/46*        (2006.01)
*A61L 27/52*        (2006.01)
(Continued)

(52) U.S. Cl.
CPC .............. *A61L 27/46* (2013.01); *A61L 27/12* (2013.01); *A61L 27/20* (2013.01); *A61L 27/52* (2013.01);
(Continued)

(58) Field of Classification Search
CPC .............. A61L 27/46; A61L 2300/414; A61L 2430/02; A61L 27/12; A61L 27/20;
(Continued)

(56) References Cited

U.S. PATENT DOCUMENTS 9,675,731 B2 *  6/2017  Ryu ......................... A61L 27/12
2009/0254194 A1 * 10/2009  Peters ..................... A61L 27/46
                                                                     623/23.61

OTHER PUBLICATIONS

Written Opinion of the International Searching Authority English translation dated Feb. 14, 2013; 4 pages.*

* cited by examiner

*Primary Examiner* — Ernst V Arnold
(74) *Attorney, Agent, or Firm* — Rosenberg, Klein & Lee

(57) ABSTRACT

The present invention relates to a carrier for growth factor related to regeneration of bone tissues that is capable of arbitrarily controlling the delivery rate of growth factors related to bone regeneration and thus especially applicable to a bone void filler in the fields of the dental or orthopedic applications.

The carrier for controlling the delivery rate of the growth factor in the present invention is composed of a hyaluronic acid hydrogel having a distribution of interconnected pores and a calcium phosphate microsphere being distributed in the pores of the hyaluronic acid hydrogel. The calcium phosphate microsphere having a porosity suitable for delivery of the growth factor is positioned into the pores of the cross-linked hyaluronic acid hydrogel to complete the carrier.

6 Claims, 3 Drawing Sheets

(51) Int. Cl.
*A61L 27/54* (2006.01)
*A61L 27/56* (2006.01)
*A61L 27/20* (2006.01)
*C08L 5/08* (2006.01)
*A61L 27/12* (2006.01)
*A61L 27/58* (2006.01)
*C01B 25/32* (2006.01)
*C08K 3/32* (2006.01)
*C08K 7/18* (2006.01)

(52) U.S. Cl.
CPC ............... *A61L 27/54* (2013.01); *A61L 27/56* (2013.01); *A61L 27/58* (2013.01); *C01B 25/327* (2013.01); *C08K 3/32* (2013.01); *C08K 7/18* (2013.01); *C08L 5/08* (2013.01); A61L 2300/414 (2013.01); A61L 2430/02 (2013.01); C01P 2004/32 (2013.01); C01P 2004/61 (2013.01); C08K 2003/325 (2013.01); C08K 2201/005 (2013.01)

(58) Field of Classification Search
CPC .......... A61L 27/52; A61L 27/54; A61L 27/56; A61L 27/58; C08L 5/08
See application file for complete search history.

US 9,925,306 B2

HYALURONIC ACID-CALCIUM PHOSPHATE COMPOSITE FOR GROWTH FACTOR SUPPORT AND METHOD FOR PRODUCING SAME

REFERENCE TO RELATED APPLICATION

This Application is being filed as a Divisional Application based on Patent Application Ser. No. 14/388,013, filed 10 Mar. 2015, currently pending.

TECHNICAL FIELD

The present invention relates to a hyaluronic acid/calcium phosphate composite for loading growth factors and a preparation method thereof and, more particularly to, a hyaluronic acid/calcium phosphate composite and a preparation method thereof, where the hyaluronic acid/calcium phosphate composite is capable of arbitrarily controlling the delivery rate of a growth factor related to bone regeneration and used as a carrier for growth factor in regeneration of bone tissue applicable to the bone void filler for dental or orthopedic applications.

BACKGROUND ART

A number of patent and non-patent documents have proposed the results of many studies on the carrier to deliver growth factors.

For example, Korean Patent Application No. 10-2008-0100315 discloses a preparation method for porous calcium phosphate granules and a manufacturing method for a functional bone graft material using the same.

However, this technology involves loading growth factors in a simple manner of adsorption, but without using a material to bind the bone morphogenetic proteins to the support, so the bone morphogenetic proteins are released in a short period of time (fast release) with the difficulty in controlling the release rate, more likely causing an adverse effect that the tissue grows excessively faster than usual in the course of tissue regeneration [Yeh, T. T., S. S Wu et al., Osteoarthritis Cartilage 15(12): 1357-1366, 2007]. In addition, the technology adopts adsorption and freeze-drying of proteins, thus more possibly ends up transforming the structure of the bone morphogenetic proteins and has the difficulty in sterilizing the bone graft material on which the bone morphogenetic proteins are adsorbed.

The carrier for growth factor is a pharmaceutical preparation injected into the human body and hence subjected to proven sterilization methods, such as gamma radiation sterilization, E-beam sterilization, or high-pressure steam sterilization, ethylene oxide (E.O.) gas sterilization, in the manufacturing process of medical equipment. These sterilization methods involve irradiation of heat or radioactive rays to have an effect on the structure of the proteins. Therefore, the bone morphogenetic proteins after the sterilization process not only fail to achieve their intended effects sufficiently but also become recognized as transformed proteins in the human body, with high possibility of causing an adverse effect [Chen, J. B. et. Al., J Biomed Mater Res A, 80(2): 435-443, 2007].

On the other hand, International Patent Application No. PCT/EP2008/005340 discloses the technology related to a composite bone repair material including a porous block type ceramic scaffold and a stabilizing polymer arranged in the support.

The ceramic scaffold is immersed in an aqueous solution of polyethylene glycol thio (PEG-thiol)containing bioactive substances, such as parathyroid hormone (PTH), bone morphogenetic protein (BMP), enamel matrix derivative (EMD), etc., and a polymer mixture of polyarm polyethylene glycol acrylate (polyarm PEG-acrylate) to form a bone repair material that contains bioactive substances. But, the polymers used in this method, that is, the aqueous solution of PEG-thiol and polyarm PEG-acrylate are free from the portion to bind the bioactive substances to the support, so it is impossible to achieve a controlled release of the growth factors as specified above. The results of the PTH release test proposed in this document show that the release of the growth factors is completed in 5.8 days. When such a release profile is applied to the bone morphogenetic proteins (BMPs) that are growth factors for bone generation and organization, the bone morphogenetic proteins (BMPs) can be released excessively fast (fast release) to cause an adverse effect on the bone generation or bone regeneration, such as generating bone in the regions other than the bone tissue or failing to achieve a fast regeneration of bone in the damaged bone tissue.

Further, International Patent Application No. PCT/IB2009/005235 discloses a bone morphogenetic composition prepared by mixing a bone morphogenetic growth factor/amphipathic anionic polysaccharide composite and at least one at least divalent cationic soluble salt and processed into an open implant in the freeze-dried form. This document suggests the use of hyaluronic acid to promote the effect of the growth factors, but no approach to the method for controlling the delivery rate of the growth factors.

In addition, Korean Patent Application No 10-2008-0038777 specifies a hyaluronic acid bone void filler composite and a preparation method thereof, which the hyaluronic acid bone void filler composite is prepared by adding a calcium phosphate derivative to a matrix including hyaluronic acid to induce bone regeneration by the osteoconductive action of the hyaluronic acid.

However, the technology disclosed in the document relates to the bone void filler used to fill in the bony voids but does not suggest any technology regarding the carrier for growth factor promoting bone generation. Moreover, the calcium phosphate compound used as a bone regeneration inducer composed of hydroxyapatite and $\beta$-TCP is prepared by the chemical precipitation reaction, and it is thus impossible to control the porosity of the bone void filler. Further, the porosity of the bone void filler cannot be controlled when the calcium phosphate compound is used as a carrier for growth factor. As the pores are not interconnected with one another, neither the growth factor can be loaded in the bone void filler nor the release rate of the growth factor can be under control. Furthermore, there possibly occurs a fast release of the growth factors. As a result, the bone void filler is not suitable as a carrier for growth factor.

In other words, as the most important thing is that the carrier for growth factor for regeneration of bone tissues can be injected into the human body, the carrier for growth factor is required to be sterilized with little toxicity. In addition, the carrier for growth factor has to be biodegradable and capable of controlling the delivery rate of the growth factors arbitrarily as suitable to the size or degree of the bone voids and reducing the adverse effect possibly caused in the case of the fast release of the growth factors. Most of all, an efficient regeneration of the bone tissues takes place when the growth factors are released suitably according to the regeneration rate of the damaged tissue and only on a confined region of the damaged tissue. However, the above-specified conventional technologies do not suggest any solution to the above-mentioned problems with the carrier for growth factor for regeneration of bone tissues and there is still a need for the carrier for growth factor for regeneration of bone tissues to solve the problems.

DISCLOSURE OF INVENTION

In order to solve the problems with the prior art, it is an object of the present invention to provide a carrier for growth factor for regeneration of bone tissue and a preparation method thereof, where the carrier for growth factor for regeneration of bone tissue is capable of loading the growth factor for regeneration of bone tissue while making it possible to control the release rate of the growth factor that helps bone regeneration, especially in the fields of dentistry and orthopedics, for example, related to the periodontal bone loss, implant peripheral bone, osteoporosis, surgery, traumatic bone damage, and so forth.

In order to achieve the object of the present invention, there is provided a hyaluronic acid/calcium phosphate composite for loading a growth factor that includes: a hyaluronic acid hydrogel having a distribution of interconnected pores and being cross-linked in the presence of a cross-linking agent; and a calcium phosphate microsphere being distributed in the pores of the hyaluronic acid hydrogel and having a size of 45 µm to 75 µm.

In accordance with the present invention, there is also provided a method for preparing a hyaluronic acid/calcium phosphate composite for loading a growth factor that includes: sintering calcium phosphate powder at 1,050° C. to 1,250° C. to obtain a spherical calcium phosphate microsphere having a size of 45 ∞m to 75 µm; and mixing the calcium phosphate microsphere with a hyaluronic acid hydrogel cross-linked in the presence of a cross-linking agent to obtain a hyaluronic acid/calcium phosphate composite for loading a growth factor.

EFFECTS OF THE INVENTION

According to the present invention, it is advantageous in that the hyaluronic acid/calcium phosphate composite is prepared using calcium and phosphate naturally present in the bone tissue and hyaluronic acid naturally present in the extracellular matrix and thus suitable to deliver growth factors related to bone regeneration and effectively useful in promoting the bone regeneration.

BEST MODES FOR CARRYING OUT THE INVENTION

Figure 1:
FIG. 1 is a mimetic diagram showing the net charge of the growth factor according to the iso-electric point of the growth factor and the pH value of the environment.

Hereinafter, the present invention will be described in further detail.

The present invention provides a carrier capable of controlling the delivery rate of the growth factor. The carrier is composed of a hyaluronic acid hydrogel having a distribution of interconnected pores and a calcium phosphate microsphere being distributed in the pores of the hyaluronic acid hydrogel. The calcium phosphate microsphere of a different porosity is positioned in the pores having a different degree of cross-linking to complete the carrier.

The first principle of the present invention to control the delivery rate of the growth factor is electrical attraction between the growth factor and the carrier. The bone morphogenetic growth factor involved in the bone regeneration has an iso-electric point of approximately 8 to 10 and takes electrically positive charges at about pH 7 that is the in-vivo environment (Refer to FIG. 1) [T. Boix et al., Journal of Inorganic Biochemistry 99 (2005), Atsushi Iwakura et al., J. thorac Cardiovasc Surg. 126: (2003), Jeroen J. J. P. et al., Tissue Engineering, Volume 13, Number 4, (2007)].

Based on the understandings of this point, the present invention employs hyaluronic acid and calcium phosphate as constituent substances of a carrier for delivering the growth factor related to bone regeneration, where the hyaluronic acid and the calcium phosphate take electrically negative charges at the in-vivo pH value. Hyaluronic acid contains functional groups such as hydroxyl groups (—OH) or carboxyl groups (—COOH) that carry electrically negative charges, and its surface takes electrically negative charges by the phosphate group (—$PO_4$) of calcium phosphate. The growth factor related to bone regeneration is loaded on the functional groups of the carrier having electrically negative charges through the electrical bonding, and the release rate of the growth factor from the carrier can be controlled according to the structure of the hyaluronic acid hydrogel and the calcium phosphate microsphere.

Further, the second principle of the present invention to control the delivery rate of the growth factor is related to the porosity of the carrier for the growth factor. The carrier for delivering the growth factor is composed of a calcium phosphate microsphere having a distribution of interconnected pores and a hyaluronic acid hydrogel having a desired porosity. When the calcium phosphate microsphere has a high porosity, the growth factor is positioned deep and wide in the central portion of the microsphere and the pores of the microsphere and released slowly. Further, with an increase in the degree of cross-linking of the hyaluronic acid hydrogel, the hydrogel has the increased porosity, higher strength and lower degradation rate. This leads to a decrease in the exposure rate of the calcium phosphate microsphere and thus makes the growth factor bound to the carrier released slowly.

In the present invention, the term "degree of cross-linking" refers to the permanent structure that individual molecules or monomer chains of the hyaluronic acid polymer are interconnected. Moreover, for the purpose to achieve the object of the present invention, the degree of cross-linking is defined as the percentage (%) weight ratio of the cross-linking agent with respect to the unit of the hyaluronic acid monomer in the cross-linked portion of the hyaluronic acid-based composition. This can be measured as the weight ratio of the hyaluronic acid monomer to the cross-linking agent (i.e., hyaluronic acid monomer: cross-linking agent).

The hyaluronic acid as used in the present invention is not specifically limited, but in general a natural substance, preferably derived from vertebrates or microorganisms. Typically, the hyaluronic acid has a molecular weight of 600,000 to 7,000,000. But, the molecular weight of the hyaluronic acid used in the present invention is preferably in the range of 1,000,000 to 5,000,000 in consideration of viscosity, degradability, and so forth.

The hyaluronic acid can be extracted from the tissues or bio-synthesized. In this regard, many documents are known (Korean Patent Nos. 1993-0001320 (Feb. 25, 1993) and 1987-0001815 (Oct. 13, 1987)). For example, the hyaluronic acid may be extracted from the tissues, such as of chicken crest, synovial fluid of joints, humane umbilical cord tissue, bovine bronchial tubes, etc. or obtained from the culture of microorganisms, such as non-hemolytic streptococcus.

The hyaluronic acid hydrogel constituting the carrier for growth factor according to the present invention is cross-linked. The porosity and pore size of the hydrogel can be controlled by adjusting the degree of cross-linking, and the retention ratio and the affinity of the growth factor to the hydrogel can be controlled by changing the structure of the hydrogel. Further, the degradation rate of the hydrogel can be under control to regulate the release rate of the growth factor through mass erosion. The hyaluronic acid hydrogel can be cross-linked in the presence of polyoxyethylene bis(glycidyl ether), 1,2,3,4-diepoxybutane, 1,2,7,8-diepoxyoctane, diethylene glycol diglycidyl ether, 1,4-butanediol diglycidyl ether, etc., preferably polyoxyethylene bis(glycidyl ether) or 1,4-butanediol diglycidyl ether.

The degree of cross-linking of the hyaluronic acid hydrogel as desirable to serve as a carrier for growth factor in the present invention is 40% or less. This is to adjust the degradation rate of the hyaluronic acid hydrogel to the initial period of bone regeneration. Generally, the initial period of bone regeneration is known to be about 2 months. For adjusting the rate of bone regeneration to this range, it is desirable for the scaffold to degrade about 2 months after installation. If the scaffold remains without degradation 3 months or more after installation, it is known to interfere with bone regeneration or bone formation. Hence, there is required a carrier having an appropriate degradation rate.

The other constituent component of the carrier of the present invention is calcium phosphate. In the present invention, calcium phosphate in the form of porous microsphere is used in order to control the delivery rate of the growth factors. The porosity of the calcium phosphate microsphere can be adjusted arbitrarily in the manufacturing process to control the affinity of the growth factor loaded on the microsphere. The present invention uses this principle to control the delivery rate of the growth factor. The porosity of the calcium phosphate microsphere can be controlled in the process to control the sintering temperature, which is preferably in the range of 1,050° C. to 1,250° C.

It is also necessary in the present invention to control the diameter of the calcium phosphate microsphere in order for the calcium phosphate microsphere to effectively function in the delivery of the growth factor. In particular, the minimum diameter of the calcium phosphate microsphere is 45 μm so as to prevent the phagocytosis of macrophages in the initial immune reaction so that the calcium phosphate microsphere can be used in the delivery of growth factor without being degraded in a short period of time. Further, the maximum diameter of the calcium phosphate microsphere is 75 μm in consideration of the pore size of the humane trabecular bone, which varies depending on the region of the human body but generally ranges from 100 μm to 300 μm.

The calcium phosphate microsphere may be prepared with monocalcium phosphate ($Ca(H_2PO_4)_2$), dicalcium phosphate ($CaHPO_4$), calcium dihydrogen phosphate ($Ca(H_2PO_4)_2$), tricalcium phosphate(TCP) ($Ca_3(PO_4)_2$), octacalcium phosphate ($Ca_8H_2(PO_4)_6 \cdot 5H_2O$), etc. The calcium phosphate microsphere prepared in the present invention is a carrier for growth factor as implanted in vivo and preferably uses β-TCP that is advantageously biodegradable, absorbed by the osteoclasts and useful in the bone regeneration when absorbed as a constituent component for bone.

In general, the growth factor related to bone regeneration may include transforming growth factor family (TGF family), epidermal growth factor (EGF), fibroblast growth factor (FGF), vascular endothelial growth factor (VEGF), and so forth. Among these, the growth factor related to bone regeneration may be the bone morphogenetic proteins (BMPs) that are an important factor for the bone regeneration in the transforming growth factor family (TGF family). Specific examples of such BMPs may include BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, etc.

FIG. 1 is a mimetic diagram showing the net charge of the growth factor according to the iso-electric point of the growth factor and the pH value of the environment. As shown in FIG. 1, the growth factor related in the bone regeneration at the iso-electric point of 8 to 10 takes electrically positive charges, so it can be loaded on the functional groups of the carrier having electrically negative charges, such as the hydroxyl group (—OH) and the carboxyl group (—COOH) of hyaluronic acid and the phosphate group (—$PO_4$) of calcium phosphate, through electrical bonding. The release rate of the growth factor in the carrier can be controlled depending on the structures of the hyaluronic acid hydrogel and the calcium phosphate microsphere.

The hyaluronic acid hydrogel that is the constituent component of the carrier to control the delivery rate of the growth factor in the present invention has a distribution of interconnecting pores. For example, hyaluronic acid having a high molecular weight of at least 1,000,000 Da is dissolved in distilled water at pH 7.0 to a content of 1 wt. % to 20 wt. % and then sufficiently reacted with 1 wt. % to 40 wt. % of a cross-linking agent, such as polyoxyethylene bis(glycidyl ether), 1,2,3,4-diepoxybutane, 1,2,7,8-diepoxyoctane, diethylene glycol diglycidyl ether, or 1,4-butanediol diglycidyl ether, to obtain a hyaluronic acid hydrogel having a degree of cross-linking in the range of 1% to 40%.

The hyaluronic acid hydrogel with a different degree of cross-linking has a different porosity, which results in a different degradation rate of the hyaluronic acid hydrogel and hence a different release rate of the growth factors bonded to the hyaluronic acid hydrogel. As can be seen from Table 1, which presents the degradation rate of the hyaluronic acid hydrogel depending on the degree of cross-linking, the degradation rate of the hyaluronic acid hydrogel is remarkably dependent upon the degree of cross-linking.

TABLE 1

Degradability of hyaluronic acid hydrogel controlled in degree of cross-linking in the presence of 100 units of enzyme for breaking down hyaluronic acid hydrogel

| Degree of cross-linking (%) | 1 | 20 | 40 |
|---|---|---|---|
| | | Degradability (%) | |
| 0 hour | 0 | 0 | 0 |
| 3 hours | 21.61 | 13.56 | 8.31 |
| 6 hours | 42.53 | 25.40 | 12.28 |
| 24 hours | 69.82 | 39.43 | 13.05 |
| 36 hours | 84.1 | 47.52 | 15.89 |
| 48 hours | 100 | 52.61 | 17.23 |

The other constituent component of the carrier for controlling the delivery rate of the growth factor in the present invention, the calcium phosphate microsphere is, for example, β-TCP that has high in-vivo affinity and is biodegradable and absorbable in vivo. Firstly, β-TCP powder is synthesized and spray-dried into spherical particles, which are then sintered at 1,050° C. to 1,250° C. to prepare porous β-TCP microspheres. The sintered β-TCP microsphere is a spherical particle having an isotropic structure and its porosity is dependent upon the sintering temperature. In other words, as can be seen from Table 2, the increase in the sintering temperature leads to a gradual reduction in the porosity of the β-TCP microsphere and hence the decreased absorption rate of the β-TCP microsphere.

Figure 2:
FIG. 2 is an SEM (Scanning Electron Microscopic) image of a β-TCP microsphere according to the sintering temperature of the β-TCP microsphere.

The surface pore structure of the β-TCP microsphere depending on the sintering temperature is shown in FIG. 2. According to FIG. 2, as the sintering temperature increases, the inter-cohesion of the surface particles becomes stronger to cause an abrupt reduction in the size and distribution of the pores connected to the exterior. Therefore, the amount of the loadable growth factor such as BMP-2 and the affinity to the growth factor are decreased with an increase in the sintering temperature. It is thus possible to prepare a carrier capable of arbitrarily controlling the release rate of the growth factor using the above-specified feature of the β-TCP microsphere.

EXAMPLES

Hereinafter, the present invention will be described in further detail with reference to the examples, which are not intended to limit the scope of the present invention.

Examples 1 to 9

1. Preparation of β-TCP Microsphere 10 g of amorphous β-TCP powder slurry dissolved in 67 ml of distilled water spry-dried at 150° C. to obtain approximately spherical β-TCP powder having an average particle size of 2 μm. The β-TCP powder put in an alumina crucible to a thickness of 10 mm is subjected to a first sintering in an electric furnace at 600° C. for one hour and then a second sintering at 1,050° C. to 1,250° C. to produce spherical β-TCP microspheres, which are then size-screened through a sieve. Among the size-sorted β-TCP microspheres, β-TCP microspheres having a size of 45 μm to 75 μm are chosen, washed with an ultrasonic washer for 30 minutes and then dried out at 70° C. for one hours to obtain the final β-TCP microspheres. The surface pore structure of the β-TCP microspheres thus obtained depending on the sintering temperature is illustrated in FIG. 2.

FIG. 2 is an SEM (Scanning Electron Microscopic) image showing the surface of the β-TCP microsphere controlled in porosity in order to regulate the delivery rate of the growth factors. Referring to the surface pore structure shown in FIG. 2, as the sintering temperature rises, the inter-cohesion of the surface particles becomes stronger to cause an abrupt reduction in the size and distribution of the pores connected to the exterior.

2. Preparation of β-TCP Microsphere 1 g of hyaluronic acid powder having a molecular weight of 1,000 kDa is dissolved in 100 ml of distilled water under agitation at 1,000 rpm for one hour. 1 to 40 wt % of 1,4-butanediol diglycidyl ether as a cross-linking agent is added to the solution, which is then adjusted to a pH 9.0. The mixture is subjected to mixing with agitator for one hour and then kept at 25° C. for 10 hours to obtain a cross-linked hyaluronic acid hydrogel.

Figure 3:
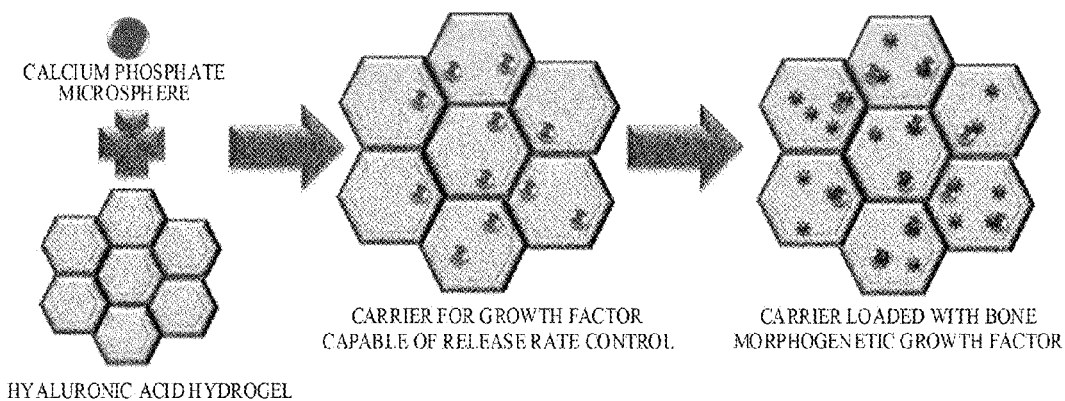
FIG. 3 is a mimetic diagram showing a carrier capable of controlling the delivery rate of the growth factor using a hyaluronic acid hydrogel and a calcium phosphate microsphere according to the present invention.

The hyaluronic acid hydrogel thus obtained is freeze-dried and then ground to powder having a particle size of 500 μm or less. After passing through a sieve, 5 g of the hyaluronic acid hydrogel powder is mixed with 5 g of the β-TCP microsphere prepared above under agitation to form 10 g of a carrier for growth factor. FIG. 3 is a mimetic diagram showing the carrier for growth factor prepared from hyaluronic acid hydrogel and calcium phosphate microspheres according to the examples of the present invention.

The porosity and water absorption of the carrier for growth factor thus prepared are presented in Table 2.

TABLE 2

Physical properties of carrier for growth factor depending on sintering temperature of β-TCP microsphere and degree of cross-linking of hyaluronic acid hydrogel

| Example | Sintering temperature (° C.) | Degree of cross-linking (%) | Porosity (%) | Water absorption (wt %) |
|---|---|---|---|---|
| 1 | 1,050 | 1 | 68.54 | 75 |
| 2 | | 20 | 66.23 | 73.1 |
| 3 | | 40 | 64.37 | 71.8 |
| 4 | 1,150 | 1 | 61.96 | 62.5 |
| 5 | | 20 | 60.24 | 56.4 |
| 6 | | 40 | 58.32 | 50 |
| 7 | 1,250 | 1 | 56.21 | 45.9 |
| 8 | | 20 | 53.58 | 43.4 |
| 9 | | 40 | 50.9 | 39.2 |

Referring to Table 2, the carrier for growth factor varies in the porosity and the water absorption depending on the sintering temperature and the degree of cross-linking.

Further, the porosity and the water absorption have an effect on the release and delivery rates of the growth factors.

Bone Morphogenetic Growth Factor (BMP-2) Loading and Release Test 100 mg of the carrier for growth factor composed of the hyaluronic acid hydrogel and the β-TCP microsphere as prepared in Example 1, 3, 6, or 9 is filled in a syringe, and 100 μl of a solution of the bone morphogenetic growth factor, BMP-2 is then sucked into the syringe. The syringe is put into connection with another syringe via a straight-line connector and then subjected to a mixing process for about five times to load the growth factor on the carrier.

100 mg of the carrier loading the bone morphogenetic growth factor, BMP-2, is added to 1 ml of a phosphate buffer solution. The buffer solution containing BMP-2 released for 1, 4, 6, or 14 days is collected as a sample. The sample thus obtained is measured in regards to the amount of BMP-2 with a BMP-2 ELISA kit using the antigen-antibody reaction. The measurement results are presented in FIG. 4.

Figure 4:
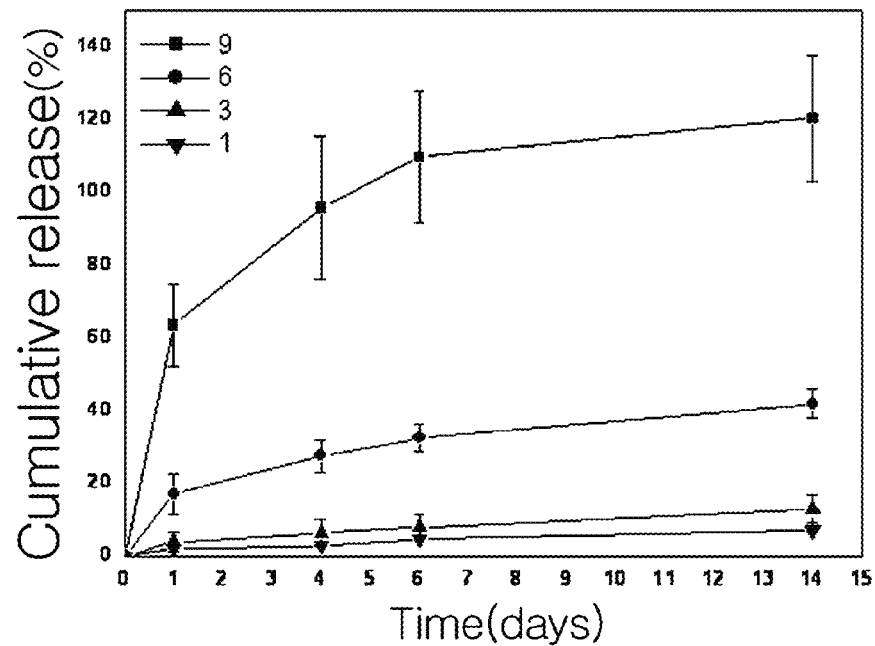
FIG. 4 shows the results of the release of growth factors related to the bone regeneration using the delivery system capable of controlling the delivery rate of the growth factor according to the present invention.

Referring to FIG. 4, the release and delivery rates of the growth factor are changed depending on the sintering temperature and the degree of cross-linking of the carrier for growth factor. In 14 days, almost all of the bone morphogenetic growth factor loaded on the carrier of Example 9 is released, while no more than 40% of the growth factor loaded on the carrier of Example 6 is released. Further, less than about 10% of the bone morphogenetic growth factor loaded on the carrier of Example 1 or 3 is released in 14 days.

The results show that BMP-2 is loaded on the carrier without deformation or damage and that the release and delivery rates of the growth factor are dependent upon the sintering temperature and the degree of cross-linking of the carrier for growth factor. This implicitly demonstrates that the release and delivery rates of the growth factor can be arbitrarily controlled.

Figure 5:
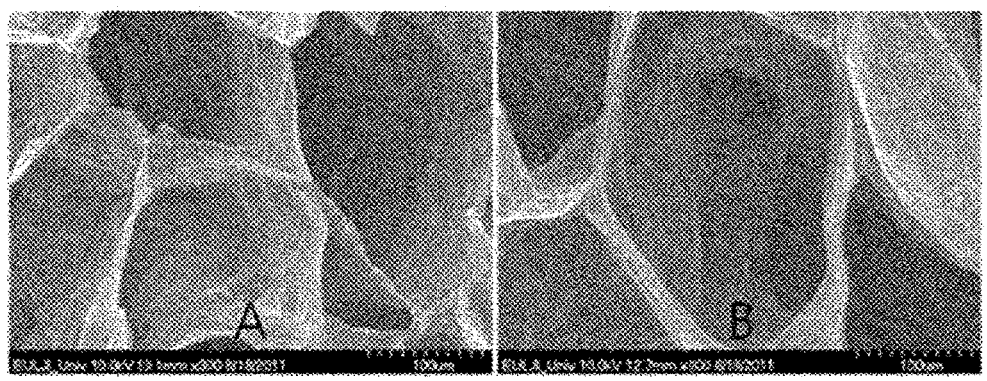
FIG. 5 is an SEM image of the hyaluronic acid hydrogel showing that the pore size is different depending on the degree of cross-linking (A: 20% cross-linking degree, B: 10% cross-linking degree).

On the other hand, FIG. 5 is an SEM image of the hyaluronic acid hydrogel showing that the pore size is dependent upon the degree of cross-linking (A: 20% cross-linking degree, B: 10% cross-linking degree), where the hyaluronic acid hydrogel has the porosity and the pore size varied depending on the degree of cross-linking. As can be seen from FIG. 5, the pore size is about 180 μm when the degree of cross-linking is 20% in (A) and about 240 μm when the degree of cross-linking is 10% in (B).

INDUSTRIAL AVAILABILITY

The hyaluronic acid/calcium phosphate composite for loading growth factors according to the present invention is capable of controlling the delivery rate of the growth factor related to bone regeneration and thus can be usefully applied as a carrier for growth factor related to the regeneration of bone tissue applicable to the bone void fillers for dental or orthopedic applications.

The present invention has been described with reference to the particular illustrative examples, which are susceptible to many changes and modifications without departing from the scope and spirit of the present. All such changes and modifications are deemed to be covered by the claims of the present invention that follow.

What is claimed is:

1. A method for preparing a hyaluronic acid/calcium phosphate composite for loading a growth factor, comprising:
    sintering calcium phosphate powder at 1,050° C. to 1,250° C. to obtain a spherical calcium phosphate microsphere having a size of 45 μm to 75 μm; and
    mixing the calcium phosphate microsphere with a hyaluronic acid hydrogel cross-linked in the presence of a cross-linking agent to obtain a hyaluronic acid/calcium phosphate composite for loading a growth factor.

2. The method as claimed in claim 1, wherein the hyaluronic acid has a molecular weight in the range of 1,000,000 to 5,000,000.

3. The method as claimed in claim 1, wherein the hyaluronic acid has a degree of cross-linking of 40% or less.

4. The method as claimed in claim 1, wherein the cross-linking agent of the hyaluronic acid is selected from the group consisting of polyoxyethylene bis(glycidyl ether), 1,2,3,4-diepoxybutane, 1,2,7,8-diepoxyoctane, diethylene glycol diglycidyl ether, and 1,4-butanediol diglycidyl ether.

5. The method as claimed in claim 1, wherein calcium phosphate constituting the calcium phosphate microsphere is selected from the group consisting of monocalcium phosphate ($Ca(H_2PO_4)_2$), dicalcium phosphate ($CaHPO_4$), calcium dihydrogen phosphate ($Ca(H_2PO_4)_2$), tricalcium phosphate ($Ca_3(PO_4)_2$), and octacalcium phosphate ($Ca_8H_2(PO_4)_6 \cdot 5H_2O$).

6. The method as claimed in claim 1, wherein the growth factor is at least one selected from the group consisting of epidermal growth factor (EGF), heparin-binding EGF-like growth factor (HB-EGF), fibroblast growth factor (FGF), vascular endothelial growth factor (VEGF), and bone morphogenetic protein (BMP), including BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, or BMP-18.

* * * * *